US009636169B2

(12) United States Patent
Allen, IV et al.

(10) Patent No.: US 9,636,169 B2
(45) Date of Patent: May 2, 2017

(54) ELECTROSURGICAL INSTRUMENT

(75) Inventors: James D. Allen, IV, Broomfield, CO (US); Ryan C. Artale, Boulder, CO (US); Kim V. Brandt, Loveland, CO (US); Dennis W. Butcher, Longmont, CO (US); Edward M. Chojin, Boulder, CO (US); Keir Hart, Lafayette, CO (US); Russell D. Hempstead, Lafayette, CO (US); Glenn A. Horner, Boulder, CO (US); Daniel A. Joseph, Golden, CO (US); Duane E. Kerr, Loveland, CO (US); Dylan R. Kingsley, Broomfield, CO (US); Peter M. Mueller, Frederick, CO (US); Jessica E. C. Olson, Frederick, CO (US); John R. Twomey, Longmont, CO (US); Jeffrey R. Unger, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1049 days.

(21) Appl. No.: 13/236,168

(22) Filed: Sep. 19, 2011

(65) Prior Publication Data

US 2013/0072927 A1    Mar. 21, 2013

(51) Int. Cl.
*A61B 18/14*    (2006.01)
*A61B 17/29*    (2006.01)
(Continued)

(52) U.S. Cl.
CPC .......... *A61B 18/1447* (2013.01); *A61B 17/29* (2013.01); *A61B 17/32* (2013.01);
(Continued)

(58) Field of Classification Search
CPC ............ A61B 2017/2926; A61B 10/06; A61B 17/1608; A61B 17/29; A61B 17/320016;
(Continued)

(56) References Cited

U.S. PATENT DOCUMENTS

D249,549 S    9/1978  Pike
4,151,846 A   5/1979  von Zeppelin et al.
(Continued)

FOREIGN PATENT DOCUMENTS

CN    201299462    9/2009
DE    2415263      10/1975
(Continued)

OTHER PUBLICATIONS

U.S. Appl. No. 08/926,869, filed Sep. 10, 1997, James G. Chandler.
(Continued)

*Primary Examiner* — Christopher D Koharski
*Assistant Examiner* — Pamela M Bays

(57) ABSTRACT

An electrosurgical forceps is provided with a shaft that extends from a housing of the electrosurgical forceps. An end effector assembly includes a pair of first and second jaw members pivotably coupled to one another via a pivot pin. One or both of the first and second jaw members may be movable from an open position for positioning tissue therebetween to a clamping position for grasping tissue. A detent is operably disposed proximal the pivot pin and extends radially outward from a proximal flange of one of the jaw members. The detent is configured to releasably engage a corresponding slot disposed on a proximal flange of the other jaw member. The detent and slot are configured to control a gap distance between the first and second jaw members when the first and second jaw members are in the clamping position.

2 Claims, 2 Drawing Sheets

(51) Int. Cl.
*A61B 17/32* (2006.01)
*A61B 18/00* (2006.01)

(52) U.S. Cl.
CPC ............ *A61B 2017/2936* (2013.01); *A61B 2017/2939* (2013.01); *A61B 2017/2946* (2013.01); *A61B 2018/0063* (2013.01); *A61B 2018/1455* (2013.01)

(58) Field of Classification Search
CPC ............ A61B 17/3201; A61B 18/1447; A61B 2018/0063; A61B 2018/1455; A61B 17/32; A61B 2017/2936; A61B 2017/2939; A61B 2017/2946
USPC .............................................. 606/46, 51, 52
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | Decarolis |
| 4,896,661 A | 1/1990 | Bogert et al. |
| 5,037,430 A | 8/1991 | Hasson |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,389,104 A * | 2/1995 | Hahnen et al. ............... 606/174 |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,887,240 B1 * | 5/2005 | Lands et al. .................... 606/51 |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 2003/0181910 A1 | 9/2003 | Dycus et al. |
| 2004/0087943 A1 * | 5/2004 | Dycus ................ A61B 17/2909 606/51 |
| 2004/0236325 A1 * | 11/2004 | Tetzlaff ............ A61B 18/1442 606/51 |
| 2005/0192598 A1 * | 9/2005 | Johnson ............ A61B 17/1608 606/148 |
| 2007/0021777 A1 * | 1/2007 | Fowler ............... A61B 17/1285 606/205 |
| 2009/0247995 A1 | 10/2009 | Bacher et al. |
| 2011/0319888 A1 * | 12/2011 | Mueller ............. A61B 18/1445 606/41 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |

(56) References Cited

FOREIGN PATENT DOCUMENTS

| | | |
|---|---|---|
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011 John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,669, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.

(56) References Cited

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 65020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.

(56) References Cited

OTHER PUBLICATIONS

Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT

BACKGROUND

Technical Field

The present disclosure relates to an electrosurgical instrument and, more particularly, to an electrosurgical instrument including an end effector having jaw members configured to maintain a specific "gap" therebetween when the jaw members are in a closed or clamping position.

Description of Related Art

Electrosurgical forceps are well known in the medical arts. For example, an electrosurgical endoscopic forceps is utilized in surgical procedures, e.g., laparoscopic surgical procedure, where access to tissue is accomplished through a cannula or other suitable device positioned in an opening on a patient. The endoscopic forceps, typically, includes a housing, a handle assembly including a movable handle, a shaft and an end effector assembly attached to a distal end of the shaft. The end effector includes jaw members configured to manipulate tissue, e.g., grasp and seal tissue. In a monopolar jaw member configuration, one jaw member includes a seal plate and a return pad is positioned on a patient. In a bipolar jaw configuration, each of the jaw members includes a respective seal plate, i.e., one seal plate functioning as an active electrode and the other seal plate functioning as the return electrode. Typically, the endoscopic forceps utilizes both mechanical clamping action and electrical energy to effect hemostasis by heating the tissue and blood vessels to coagulate, cauterize, seal, cut, desiccate, and/or fulgurate tissue. As is known in the art, to achieve a tissue seal a specific gap needs to be maintained between the jaw members when they are in a clamping position and tissue is positioned therebetween.

In order to maintain a specific gap between the jaw members when tissue is grasped therebetween, one or more stop members may be positioned along one or both seal flanges of the seal plate(s). In certain instances, the stop members may be made from one or more insulative or non-conductive materials, such as, for example, ceramic. The stop members may be secured to the seal plates via one or more suitable securement methods. For example, and in certain instances, the stop members may be secured to a seal flange of a seal plate utilizing one or more suitable adhesives, e.g., curable adhesives. However, this technique is typically complicated and requires specialty equipment/processes that increase the manufacturing cost of the seal plates, and, thus, the overall manufacturing costs of the electrosurgical instrument. Moreover, the stop member(s) may be vulnerable to shear stress failure due to the nature of the adhesive. That is, there exists the possibility of the adhesive not curing properly and succumbing to the shear stresses that may be present during an electrosurgical process, i.e., during the grasping and subsequent sealing of tissue. Further, positioning the stop members on the seal flange(s) of the seal plate(s) decreases the amount of functionable or useable sealing flange area of the seal plate. That is, the insulative nature of the stop members impedes or prevents sealing tissue that is positioned directly about the stop members.

SUMMARY

According to an aspect of the present disclosure, an electrosurgical forceps is provided. The electrosurgical forceps includes an end effector assembly that includes a pair of first and second jaw members that are pivotably coupled to one another via a pivot pin. One or both of the first and second jaw members may be movable from an open position for positioning tissue therebetween to a clamping position for grasping tissue. A detent is operably disposed proximal the pivot pin and extends radially outward from a proximal flange of one of the jaw members. The detent is configured to releasably engage a corresponding slot disposed on a proximal flange of the other jaw member. The detent and slot are configured to control a gap distance between the first and second jaw members when the first and second jaw members are in the clamping position.

According to an aspect of the present disclosure, the slot may include a generally arcuate configuration that is configured to accommodate pivotable movement of the movable jaw member. In certain instances, the slot may include an opening that is configured to receive the detent and may be defined by two sidewalls joined by a distal wall. The detent may be configured to contact the distal wall to maintain a predetermined gap distance between the first and second jaw members when the first and second jaw members are in the clamping position.

According to another aspect of the present disclosure, an electrosurgical forceps is provided with a shaft that extends from a housing of the electrosurgical forceps. A longitudinal axis is defined through the shaft. An end effector assembly operably coupled to a distal end of the shaft includes a pair of first and second jaw members pivotably coupled to one another via a pivot pin. The first and second jaw members movable from an open position for positioning tissue therebetween to a clamping position for grasping tissue. Each of the first and second jaw members includes a respective cam slot configured to house a cam pin therein such that the cam pin is movable within the cam slots to move each of the first and second jaw members from the open to clamping position. In certain instances, it may prove advantageous to provide cam slots that are angled with respect to one another. A proximal most position of each of the cam slots includes a back wall whereupon contact between the cam pin and the back wall of the respective cam slots corresponds to a desired gap distance between the first and second jaw members when the first and second jaw members are in the clamping position. In certain instances, the proximal most position of each of the cam slots may be aligned along a common axis.

BRIEF DESCRIPTION OF THE DRAWING

Various embodiments of the present disclosure are described hereinbelow with references to the drawings, wherein.

DETAILED DESCRIPTION

Figure 1:
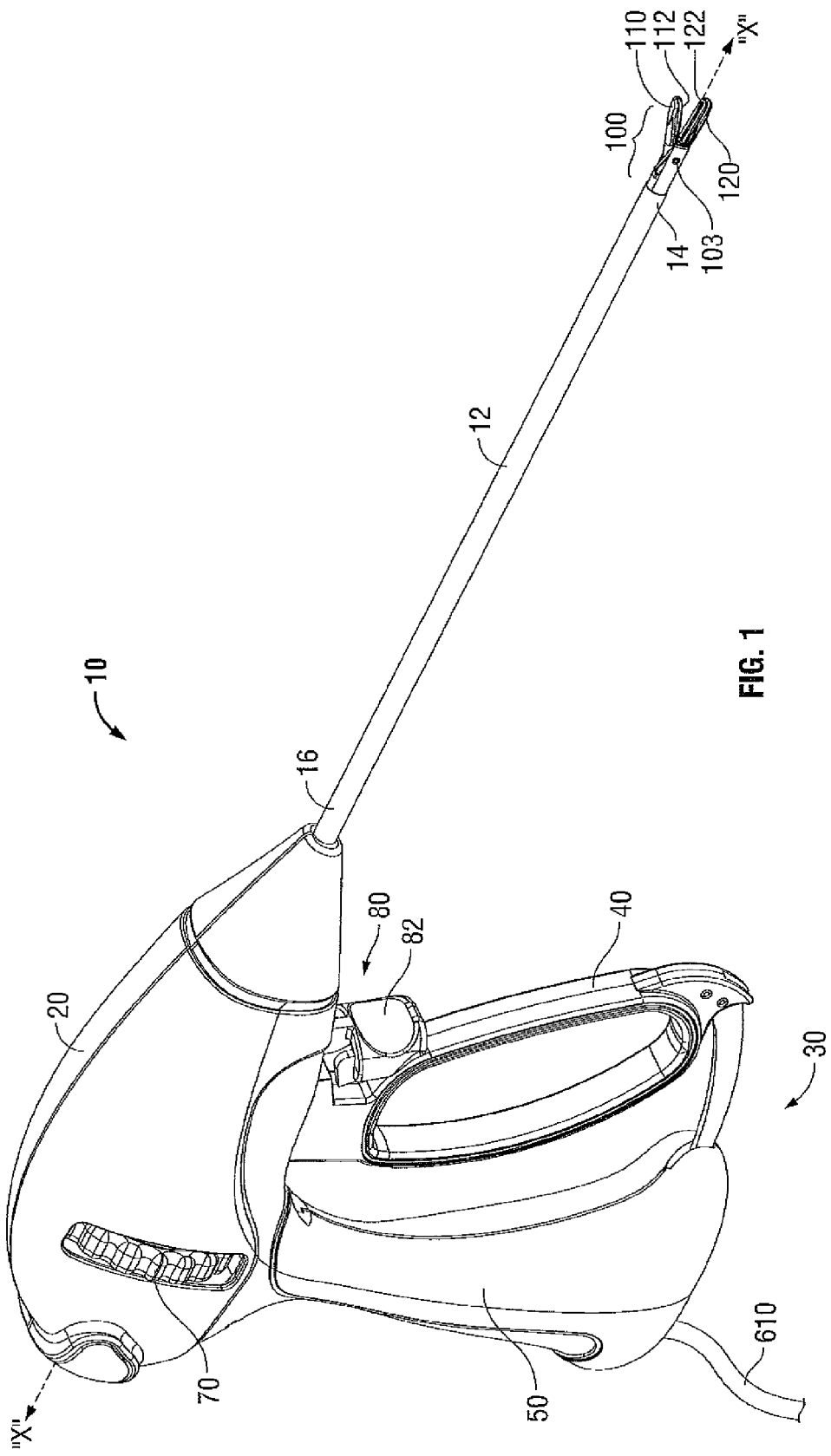
FIG. 1 is a perspective view of an electrosurgical forceps according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, an electrosurgical endoscopic forceps 10 (forceps 10) is provided having a longitudinal axis "X-X" defined therethrough and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the jaw members 110 and 120 of end effector assembly 100.

Rotating assembly 70 is rotatable in either direction about a longitudinal axis "X-X" to rotate end effector 100 about longitudinal axis "X-X." Housing 20 houses the internal working components of forceps 10, such as a drive assembly (not shown), working components of the handle assembly, electrical raceways associated with the cable 610, and other working components therein.

With continued reference to FIG. 1, handle assembly 30 includes fixed handle 50 and a moveable handle 40. Fixed handle 50 is integrally associated with housing 20 and handle 40 is moveable relative to fixed handle 50. Moveable handle 40 of handle assembly 30 is ultimately connected to the drive assembly that, together, mechanically cooperate to impart movement of jaw members 110 and 120 between a spaced-apart or open position and an approximated or clamping position to grasp tissue disposed between jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Continuing with reference with FIG. 1, end effector assembly 100 is shown attached at a distal end 14 of shaft 12 and includes opposing jaw members 110 and 120. Each of jaw members 110 and 120 includes an opposed electrically conductive tissue sealing surface 112, 122, respectively. End effector assembly 100 is designed as a unilateral assembly, i.e., jaw member 120 is fixed relative to shaft 12 and jaw member 110 is moveable about a pivot 103 relative to shaft 12 and fixed jaw member 120. However, end effector assembly 100 may alternatively be configured as a bilateral assembly, i.e., where both jaw member 110 and jaw member 120 are moveable about pivot 103 relative to one another and to shaft 12, see FIG. 4 for example. In some embodiments, a knife assembly (not shown) is disposed within shaft 12 and a knife channel (not shown) is defined within one or both jaw members 110, 120 to permit reciprocation of a knife blade (not shown) therethrough, e.g., via activation of trigger 82 of trigger assembly 80.

Figure 2:
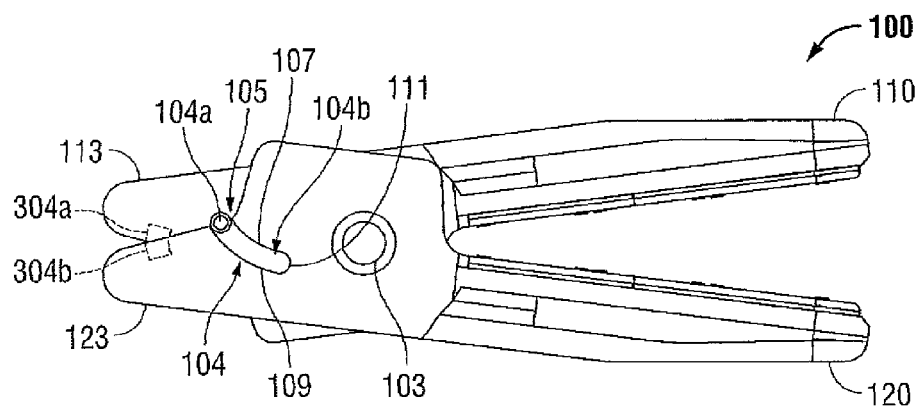
FIG. 2 is schematic, plan view of a pair of jaw members associated with the electrosurgical forceps depicted in FIG. 1.
Figure 3:
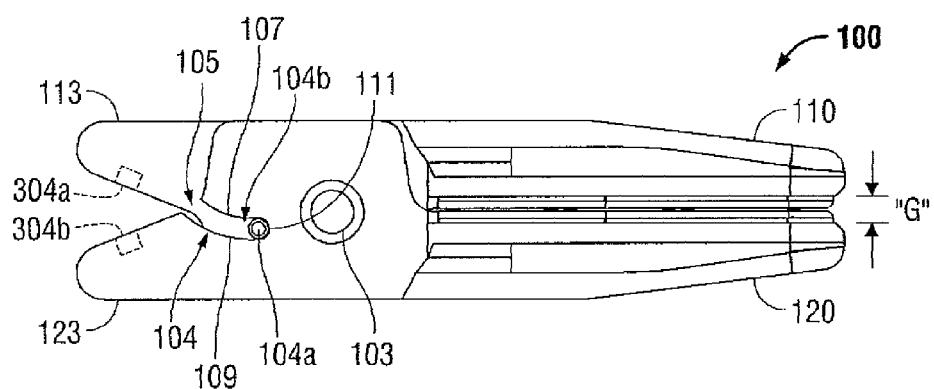
FIG. 3 is schematic, plan view of the jaw members depicted in FIG. 2 in a closed configuration.

With reference now to FIGS. 2 and 3, in addition to the respective seal plates 112 and 122, jaw members 110 and 120 each include respective proximal flanges 113 and 123. In the embodiment illustrated in FIGS. 2 and 3, proximal flanges 113 and 123 are configured to facilitate moving one (unilateral jaw configuration) or both (bilateral jaw configuration) of the jaw members 110 and 120 from the open configuration to the clamping position and maintaining a specific gap distance "G" therebetween when the jaw members 110 and 120 are in the clamping position. In particular, the proximal flanges 113 and 123 are configured to provide a "hard stop" configuration, i.e., the proximal flanges 113 and 123 (or portion(s) thereof) are configured to contact each other to limit movement of the jaw members 110 and 120 toward one another. With this purpose in mind, one or both of the jaw members 110 and 120 includes one or more stop members 104 thereon.

With continued reference to FIGS. 2 and 3, and for illustrative purposes, stop member 104 is shown operably disposed on the proximal flange 113 of the jaw member 110, i.e., stop member 104 is operably disposed at a position that is proximal relative to the pivot pin 103 to control a gap distance between the jaw members 110 and 120 when the jaw members 110 and 120 are in the clamping position. Alternatively, stop member 104 may be operably disposed on the proximal flange 123 of the jaw member 120. In this particular embodiment, and in contrast to the embodiment shown in FIG. 4, stop member 104 is independent of any camming or actuating elements of the jaw members 110 and 120.

Stop member 104 may be made from any suitable material including, but not limited to, plastic, ceramic, metal, etc. For the purposes of the present disclosure, it may be assumed that stop member 104 is made from a relatively rigid plastic. Stop member 104 may be monolithically formed with the jaw member 110 or stop member 104 may be formed and, subsequently, coupled or affixed (via one or more suitable affixation methods) to the jaw member 110. Stop member 104 may be configured as needed to provide a required or requisite gap distance between the jaw members 110 and 120 when the jaw members 110 and 120 are in the clamping position.

In particular, and in the embodiment illustrated in FIGS. 2 and 3, stop member 104 is in the form of a detent 104a that is configured to releasably engage a corresponding slot 104b operably defined on the proximal flange 123 of the jaw member 120. More particularly, detent 104a extends radially outward from the proximal flange 113 of jaw member 110 and is configured to releasably engage the corresponding slot 104b that extends radially inward from the proximal flange 123 of jaw member 120.

Slot 104b includes a relatively arcuate configuration of suitable proportion (FIGS. 2 and 3) to accommodate the pivotable movement of the jaw member 110 when the jaw member 110 moves from the open to clamping position and vice versa. Slot 104b is defined by an opening 105 and three walls including top sidewall 107, bottom sidewall 109 and distal wall 111. Distal wall 111 joins adjoining respective top and bottom sidewalls 107 and 109. The dimensions of the slot 104b are proportioned to achieve a requisite gap distance "G" between the jaw members 110 and 120. In particular, the distance that detent 104a moves within slot 104b to contact the distal wall 111 corresponds to a specific gap distance between the jaw members 110 and 120, respectively, when the jaw members 110 and 120 are in the clamping position (as best seen FIG. 3). For example, movement of detent 104a within slot 104b equal to about 2 mm may correspond to a gap distance between the jaw members 110 and 120, respectively, equal to about 0.001 inches to about 0.006 inches. In other embodiments, the gap distance between the jaw members 110 and 120 may be less than 0.001 inches and greater than 0.006 inches. As can be appreciated, the specific distance that detent 104a moves within slot 104b may be altered to achieve a specific gap distance "G" between the jaw members 110 and 120 when the jaw members 110 and 120 are in the clamping position.

In certain embodiments, the proximal flange 123 of the jaw member 120 may be configured without a corresponding slot 104b. In this instance, detent 104a may be configured to simply contact or engage the proximal flange 123 of the jaw member 120. Alternatively, it may prove advantageous to have each proximal flange 113 and 123 include a respective detent 304a and 304b (shown in phantom in FIG. 2) extending radially outward therefrom and configured to contact each other when the jaw members 110 and 120 are in the clamping position. The specific configuration of the proximal flanges 113, 123 of the jaw members 110 and 120 may depend on the specific needs of a manufacturer, a specific surgical procedure, a specific gap distance "G" desired between the jaw members 110 and 120, etc.

Positioning the stop member 104 proximal the pivot 103 or "off" the seal plates 112 and 122 when compared to conventional forceps that, as noted above, typically, have one or more stop members positioned or secured to the seal plates, allows for greater surface area contact or coverage between the seal plates 112 and 122 and tissue when tissue is positioned between the jaw members and the jaw members 110 and 120 are in the clamping position. Moreover, the chances or the likelihood of the stop member 104 detaching from the seal plate are eliminated. Moreover, the contact or surface area between the seal plates 112 and 122 and tissue is greatly increased, which, in turn, may provide a better tissue seal, e.g., a more uniform and consistent tissue seal. Further, positioning the stop member 104 proximal to the pivot 103 or "off" the seal plates 112 and 122, may reduce the cost of manufacturing the jaw members 110 and 120 and/or the seal plates 112 and 122, which, in turn, may reduce the overall cost of manufacturing the forceps 10.

In use, jaw members 110 and 120 are, initially, in an open configuration to receive or position tissue therebetween (see FIGS. 1 and 2). Proximal movement of the movable handle 40 actuates or drives a drive rod (not shown), which, in turn, moves jaw member 110 from the open configuration to the clamping position. As jaw member 110 moves from the open configuration to the clamping position, detent 104a moves within the confines of the slot 104b until such time that the detent 104a contacts the distal wall 111. Contact between the distal wall 111 of the detent 104a and slot 104b maintains a desired gap distance "G" between the jaw members 110 and 120.

Figure 4:
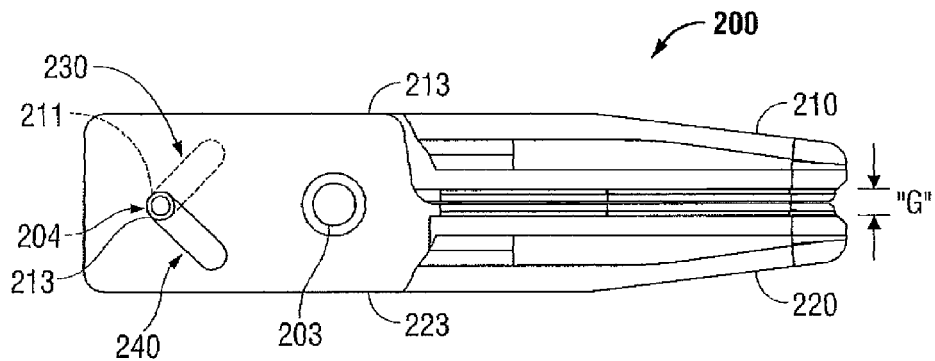
FIG. 4 is schematic, plan view of a pair of jaw members according to another embodiment of the present disclosure.

With reference to FIG. 4, an end effector 200 including jaw members 210 and 220 according to an alternate embodiment of the present disclosure is illustrated. Unlike the jaw members 110 and 120 each of jaw members 210 and 220 is configured to move from the open configuration to the clamping position, i.e., a bilateral jaw design. In the embodiment illustrated in FIG. 4, the end effector utilizes a "hard stop configuration" including a pair of cam slots 230 and 240 are operably disposed on respective proximal flanges 213 and 223 of the jaw members 210 and 220. Cam slots 230 and 240 are angled with respect to one another such that a proximal most position of each of the cam slots 230 and 240 is aligned along a common axis (as best seen in FIG. 3).

A cam pin 204 is operably disposed within the cam slots 230 and 240 and is operable to move the jaw members 210 and 220 from the open configuration to the closed configuration. In particular, cam pin 204 is operably coupled to the drive rod (not shown) to provide proximal and distal movement of the cam pin 204 within the cam slots 230 and 240. Cam pin 204 is configured to contact proximal walls 211 and 213 of the respective cam slots 230 and 240. The proximal walls 211 and 213 function similar to that of the distal wall 111 of the intent 104b. That is, when cam pin 204 is moved a predetermined distance within the cam slots 230 and 240 and contacts the respective proximal walls 211 and 213 thereof, a predetermined jaw gap distance "G" is maintained between the jaw members 210 and 220.

In use, jaw members 210 and 220 are, initially, in an open configuration to receive or position tissue therebetween. Proximal movement of the movable handle 40 actuates or drives the drive rod, which, in turn, moves jaw members 210 and 220, via the cam pin 204, from the open configuration to the clamping position. As jaw members 210 and 220 move from the open configuration to the clamping position, cam pin 204 moves within the confines of the cam slots 230 and 240 until such time that the cam pin 204 contacts the proximal walls 211 and 213. Contact between the proximal wall 211 and 213 of the cam slots 230 and 240 maintains a desired jaw gap distance "G" between the jaw members 210 and 220. As can be appreciated, the unique configuration of the cam pin 204 and cam slots 230 and 240 overcomes the aforementioned drawbacks that are, typically, associated with conventional forceps.

From the foregoing and with reference to the various figure drawings, those skilled in the art will appreciate that certain modifications can also be made to the present disclosure without departing from the scope of the same. For example, in certain instances, one or more springs may be operably associated with either of the aforementioned end effectors 100 and 200. The one or more springs may be configured to provide a specific closure force at the jaw members, 110, 210 and 120, 220.

While the aforementioned "hard stop" configurations have been described in terms of use with an endoscopic forceps 10, it is within the purview of the present disclosure that the aforementioned "hard stop" configurations may be utilized with various surgical instruments that implement a jaw configuration, e.g., open forceps, graspers, and the like, and that require specific control of a distance between the jaw members when the jaw members are in a clamping or closed configuration. As can be appreciated, the aforementioned "hard stop" configurations may require alteration to accommodate the specific surgical instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   an end effector assembly including a pair of first and second jaw members each including a distal body and a proximal flange, the proximal flanges pivotably coupled to one another via a pivot pin, at least one of the first and second jaw members movable from an open position for positioning tissue therebetween to a clamping position for grasping tissue, wherein, in the clamping position, the distal bodies are spaced-apart from each other to define at least a minimum gap distance therebetween;

a detent positioned proximal of the pivot pin, the detent disposed on and extending outwardly from the proximal flange of one of the first and second jaw members; and a corresponding slot defined through the proximal flange of the other of the first and second jaw members, the slot defining an open proximal end providing access to the slot, a closed distal end opposing the open proximal end, and a pair of side walls extending between the open proximal end and the closed distal end, wherein the detent is configured to move from a position outside the slot, through the open proximal end of the slot into the slot, through the slot, and to bottom out within the closed distal end of the slot upon movement of the first and second jaw members towards one another to a position wherein the distal bodies define the minimum gap distance therebetween, thereby inhibiting further movement of the distal bodies towards each other.

2. An electrosurgical forceps according to claim 1, wherein the slot includes a generally arcuate configuration that is configured to accommodate pivotable movement of the movable jaw member.

\* \* \* \* \*